US007763591B2

(12) United States Patent
Morishita (10) Patent No.: US 7,763,591 B2
(45) Date of Patent: Jul. 27, 2010

(54) HEPATOCYTE GROWTH FACTOR GENE THERAPY FOR PARKINSON'S DISEASE

(75) Inventor: Ryuichi Morishita, Osaka (JP)

(73) Assignee: AnGes MG, Inc., Shinsenri-Higashimachi, Toyonaka-shi, Osaka (JP)

( * ) Notice: Subject to any disclaimer, the term of this patent is extended or adjusted under 35 U.S.C. 154(b) by 766 days.

(21) Appl. No.: 10/495,132

(22) PCT Filed: Nov. 27, 2002

(86) PCT No.: PCT/JP02/12388

§ 371 (c)(1),
(2), (4) Date: May 7, 2004

(87) PCT Pub. No.: WO03/045439

PCT Pub. Date: Jun. 5, 2003

(65) Prior Publication Data

US 2004/0265283 A1    Dec. 30, 2004

(30) Foreign Application Priority Data

Nov. 28, 2001  (JP)  ............................. 2001-363289
Oct. 28, 2002  (JP)  ............................. 2002-312546

(51) Int. Cl.
*A01N 43/04*  (2006.01)
*A01N 63/00*  (2006.01)
*A01N 65/00*  (2006.01)
*A61K 31/70*  (2006.01)

(52) U.S. Cl. .................................... 514/44 R; 424/93.1
(58) Field of Classification Search .................. None
See application file for complete search history.

(56) References Cited

U.S. PATENT DOCUMENTS 6,248,722 B1    6/2001  Morishita et al.

FOREIGN PATENT DOCUMENTS

| EP | 0 722 737 | 7/1996 |
| EP | 0 847 757 | 6/1998 |
| EP | 1 132 098 | 9/2001 |
| EP | 1 142 590 | 10/2001 |
| JP | 3-72883 | 3/1991 |
| WO | WO 97/07824 | 3/1997 |
| WO | WO 99/36103 | 7/1999 |
| WO | WO 01/26694 | 4/2001 |

OTHER PUBLICATIONS

Verma, et al. (1997) Nature, 389: 239-42.*
Pfeifer and Verma (2001) Annu. Rev. Genomics. Hum. Genet. 2:177-211.*
Johnson-Saliba et al. (2001) Curr. Drug. Targets 2:371-99.*
Shoji et al. (2004) Current Pharmaceutical Design 10 :785-796.*
Deonarain (1998) Expert Opin. Ther. Pat., 8: 53-69.*
Eck et al. (1996) Goodman & Gilman's The Pharmacological Basis of Therapeutics, McGraw-Hill, New York, NY., pp. 77-101.*
Gorecki (2001) Expert Opin. Emerging Drugs 6(2): 187-98.*
Kahle et al. (2001) Emerging Therapeutic Targets, 5(1): 125-132.*
Hayashi, et al. (2001) Gene Therapy, 8:1167-73.*
Tsuboi, et al. (2002) Acta Neurol. Scand., 106: 99-103.*
Schober (2004) Cell Tissue Res., 318: 215-24.*
Wolff (1997) Neuromuscul. Disord., 7(5): 314-18.*
Wolff, et al. (1990) Science, 247: 1465-68.*
Langston (1999) Ann. Neurol., 46: 598-605.*
McGreer (2003) Ann. Neurol., 54:599-604.*
Castro, et al. (2001) Histol. Histopathol., 16(4): 1225-38 Abstract Only.*
Romrell, et al. (2003) Exoert Opinion in Pharmacotherapy, 4(10): 1747-61.*
Åkerud et al., "Neuroprotection through delivery of glial cell line-derived neurotrophic factor by neural stem cells in a mouse model of Parkinson's disease," *J. Neurosci. 21*, 8108-18, Oct. 15, 2001.
Ben-Shachar et al., "Role of iron and iron chelation in dopaminergic-induced neurodegeneration: implication for Parkinson's disease," *Ann. Neural. 32 Suppl.*, S105-110, 1992 (abstract).
Choi-Lundberg et al., "Dopaminergic neurons protected from degeneration by GDNF gene therapy," *Science 275*, 838-41, Feb. 7, 1997 (abstract).
Choi-Lundberg et al., "Behavioral and cellular protection of rat dopaminergic neurons by an adenoviral vector encoding glial cell line-derived neurotrophic factor," *Exp. Neural. 154*, 261-75, Dec. 1998 (abstract).
Connor, "Adenoviral vector-mediated delivery of glial cell line-derived neurotrophic factor provides Neuroprotection in the aged parkinsonian rat," *Clin. Exp. Pharmacol. Physiol 28*, 896-900, Nov. 2001 (abstract).
Costa et al., "Nicotine prevents striatal dopamine loss produced by 6-hydroxydopamine lesion in the substantia nigra," *Brain Res. 888*, 336-42, Jan. 12, 2001 (abstract).
Glinka et al., "Mechanism of 6-hydroxydopamine neurotoxicity," *J. Neural Transm. [Suppl.] 50*, 55-66, 1997.
Grünblatt et al., "MPTP and 6-hydroxydopamine-induced neurodegeneration as models for Parkinson's disease: neuroprotective strategies," *J. Neurol 247 [Suppl. 2]*, II/95-II/102, 2000.
He et al., "Minocycline inhibits microglial activation and protects nigral cells after 6-hydroxydopamine injection into mouse striatum," *Brain Res. 909*, 187-93, 2001.
Kearns et al., "GDNF Protection against 6-OHDA: Time Dependence and Requirement for Protein Synthesis," *J. Neurosci. 17*, 7111-18, Sep. 15, 1997.

(Continued)

*Primary Examiner*—Robert M Kelly
(74) *Attorney, Agent, or Firm*—Banner & Witcoff, Ltd.

(57) ABSTRACT

The present invention provides a therapeutic agent containing as an active ingredient an HGF gene used for the therapy of neurodegenerative diseases such as Parkinson's disease, Alzheimer's disease, spinal cord injury, diabetic peripheral neuritis, and ischemic cerebrovascular disorders such as cerebral infarction, cerebral hemorrhage, etc. More specifically, the present invention provides a therapeutic agent for neurodegenerative diseases, containing a hepatocyte growth factor (HGF) gene as an active ingredient.

12 Claims, 4 Drawing Sheets

OTHER PUBLICATIONS

Murray et al., "Evaluation of the mGluR2/3 agonist LY379268 in rodent models of Parkinson's disease," *Phamacol. Biochem. Behav.* 73, 455-66, Sep. 2002 (abstract).

National Institute of Neurological Disorders and Stroke, "Neuroprotective Agents for Clinical Trials," http://www.ninds.nig.gov/funding/research/parkinsonsweb/drug_summaries, 2 pages, printed Mar. 23, 2007.

Oiwa et al., "Dopaminergic Neuroprotection and regeneration by neurturin assessed by using behavioral, biochemical and histochemical measurements in a model of progressive Parkinson's disease," *Brain Re. 947*, 271-83, Aug. 30, 2002 (abstract).

Ravina et al., "Neuroprotective agents for clinical trials parkinson's disease," *Neurology 60*, 1234-40, Apr. 2003.

Strelau et al., "Growth/Differentiation factor-15/Macrophage Inhibitory Cytokine-1 Is a Novel Trophic Factor for Midbrain Dopaminergic Neurons In Vivo," *J. Neurosci. 20*, 8597-603, Dec. 1, 2000.

Tolwani et al., "Experimental Models of Parkinson's Disease: Insights from Many Models," *Laboratory Animal Science 49*, 363-71, Aug. 1999.

Van Kampen et al., "Dopamine transporter function assessed by antisense knockdown in the rat: protection from dopamine neurotoxicity," *Synapse 37*, 171-78, Sep. 1, 2000 (abstract).

Wang et al., "Vitamin D(3) attenuates 6-hydroxydopamine-induced neurotoxicity in rats," *Brain Res. 15*, 67-75, Jun. 15, 2001.

Hamanoue et al., "Neurotrophic Effect of Hepatocyte Growth Factor on Central Nervous System Neurons In Vitro," *J. Neurosci. Res. 43*, 554-64,1996.

Bensadoun et al., "Lentiviral vectors as a gene delivery system in the mouse midbrain: cellular and behavioral improvements in a 6-OHDA model of Parkinson's disease using GDNF," Exp Neurol. Jul. 2000;164(1):15-24.

Björklund et al., "Towards a neuroprotective gene therapy for Parkinson's disease: use of adenovirus, AAv and lentivirus vectors for gene transfer of GDNF to the nigrostriatal system in the rat Parkinson model," Brain Res. Dec. 15, 2000;886(1-2):82-98.

Blandini et al., "Neuroprotective effect of rasagiline in a rodent model of Parkinson's disease," Exp Neurol. Jun. 2004;187(2):455-9.

Boess & Martin, "Molecular biology of 5-HT receptors," Neuropharmacology. Mar.-Apr. 1994;33(3-4):275-317.

Bohn et al., "Gene transfer for neuroprotection in animal models of Parkinson's disease and amyotrophic lateral sclerosis," Novartis Found Symp. 2000;231:70-89; discussion 89-93.

Bové et al., "Toxin-Induced Models of Parkinson's Disease," *NeuroRx 2*, 484-94, Jul. 2005.

Ceravolo et al., "Assessing neuroprotection in Parkinson's disease: from the animal models to molecular neuroimaging in vivo," J Neural Transm Suppl. 2006;(71):133-41.

Costa et al., "Nicotine prevents striatal dopamine loss produced by 6-hydroxydopamine lesion in the substantia nigra," Brain Res. Jan. 12, 2001;888(2):336-342.

Costantini et al., "Immunophilin ligands can prevent progressive dopaminergic degeneration in animal models of Parkinson's disease," Eur J Neurosci. Mar. 2001;13(6):1085-92.

Cunningham & Su, "Astrocyte delivery of glial cell line-derived neurotrophic factor in a mouse model of Parkinson's disease," Exp Neurol. Apr. 2002;174(2):230-42.

De Keyser et al., "Dopamine agonists used in the treatment of Parkinson's disease and their selectivity for the D1, D2, and D3 dopamine receptors in human striatum," Prog Neuropsychopharmacol Biol Psychiatry. Nov. 1995;19(7):1147-54.

Dethy et al., "Pergolide potentiates L-DOPA-induced dopamine release in rat striatum after lesioning with 6-hydroxydopamine," J Neural Transm. 1999;106(2):145-58.

Emborg, "Evaluation of animal models of Parkinson's disease for neuroprotective strategies," J Neurosci Methods. Oct. 30, 2004;139(2):121-43.

Fukuzaki et al., "Effects of ropinirole on various parkinsonian models in mice, rats, and cynomolgus monkeys," Pharmacol Biochem Behav. Mar. 2000;65(3):503-8.

Georgievska et al., "Neuroprotection in the rat Parkinson model by intrastriatal GDNF gene transfer using a lentiviral vector," Neuroreport. Jan 21, 2002;13(1):75-82.

Hirsch et al., "Animal models of Parkinson's disease in rodents induced by toxins: an update," J Neural Transm Suppl. 2003;(65):89-100.

Hong et al., "Pergolide Is an Inhibitor of Voltage-Gated Potassium Channels, Including Kv1.5, and Causes Pulmonary Vasoconstriction," Circulation. Aug. 29, 2005; [Epub ahead of print].

Howells et al., "Stress reduces the neuroprotective effect of exercise in a rat model for Parkinson's disease," Behav Brain Res. Dec. 7, 2005;165(2):210-20. Epub Sep. 12, 2005.

Iida et al., "Dopamine D2 receptor-mediated antioxidant and neuroprotective effects of ropinirole, a dopamine agonist," Brain Res. Aug. 14, 1999;838(1-2):51-9.

Ikeda et al., "Neuroprotection by adenosine A2A receptor blockade in experimental models of Parkinson's disease," J Neurochem. Jan. 2002;80(2):262-70.

Klockgether et al., "Effects of the antiparkinsonian drug budipine on central neurotransmitter systems," Eur J Pharmacol. Apr. 22, 1996;301(1-3):67-73.

Knoll, "R-(–)-deprenyl (Selegiline, Movergan) facilitates the activity of the nigrostriatal dopaminergic neuron," J Neural Transm Suppl. 1987;25:45-66.

Lange et al., "Biochemical actions of 1-deprenyl (selegiline)," Clin Pharmacol Ther. Dec. 1994;56(6 Pt 2):734-41; Knoll, "R-(–)-deprenyl (Selegiline, Movergan) facilitates the activity of the nigrostriatal dopaminergic neuron," J Neural Transm Suppl. 1987;25:45-66.

Liu et al., "Bromocriptine protects against delayed neuronal death of hippocampal neurons following cerebral ischemia in the gerbil," J Neurol Sci. Mar. 1995;129(1):9-14.

Lundblad et al., "Pharmacological validation of a mouse model of 1-DOPA-induced dyskinesias," Exp Neurol. Jul. 2005;194(1):66-75 (author produced version).

Marin et al., "Early administration of entacapone prevents levodopa-induced motor fluctuations in hemiparkinsonian rats," *Exp. Neurol. 192*, 184-93, Mar. 2005.

Millan et al., "Differential actions of antiparkinson agents at multiple classes of monoaminergic receptor. I. A multivariate analysis of the binding profiles of 14 drugs at 21 native and cloned human receptor subtypes," J Pharmacol Exp Ther. Nov. 2002;303(2):791-804.

Mochizuki et al., "An AAV-derived Apaf-1 dominant negative inhibitor prevents MPTP toxicity as antiapoptotic gene therapy for Parkinson's disease," Proc Natl Acad Sci U S A. Sep. 11, 2001;98(19):10918-23. Epub Sep. 4, 2001.

Muramatsu et al., "Behavioral recovery in a primate model of Parkinson's disease by triple transduction of striatal cells with adeno-associated viral vectors expressing dopamine-synthesizing enzymes," Hum Gene Ther. Feb. 10, 2002;13(3):345-54.

Murray et al., "Evaluation of the mGluR2/3 agonist LY379268 in rodent models of Parkinson's disease," Pharmacol Biochem Behav. Sep. 2002;73(2):455-66.

Oiwa et al., "Dopaminergic neuroprotection and regeneration by neurturin assessed by using behavioral, biochemical and histochemical measurements in a model of progressive Parkinson's disease," Brain Res. Aug. 30, 2002;947(2):271-83.

Palfi et al., "Lentivirally Delivered Glial Cell Line-Derived Neurotrophic Factor Increases the Number of Striatal Dopaminergic Neurons in Primate Models of Nigrostriatal Degeneration," J Neurosci. Jun. 15, 2002;22(12):4942-54.

Park et al., "Protective effects of fustin, a flavonoid from Rhus verniciflua Stokes, on 6-hydroxydopamine-induced neuronal cell death," Exp Mol Med. Jun. 30, 2007;39(3):316-26.

Piallat et al., "Subthalamic nucleus lesion in rats prevents dopaminergic nigral neuron degeneration after striatal 6-OHDA injection: behavioural and immunohistochemical studies," Eur J Neurosci. Jul. 1996;8(7):1408-14.

Salonen et al., "Monoamine oxidase B inhibitor selegiline protects young and aged rat peripheral sympathetic neurons against 6-hydroxydopamine-induced neurotoxicity," Acta Neuropathol (Berl). 1996;91(5):466-74.

Schneider et al., "Dopamine receptors: effects of chronic L-dopa and bromocriptine treatment in an animal model of Parkinson's disease," Clin Neuropharmacol. 1984;7(3):247-57.

Shen et al., "Molecular cloning and expression of a 5-hydroxytryptamine7 serotonin receptor subtype," J Biol Chem. Aug. 25, 1993;268(24):18200-4.

Shimohama et al., "Disease model: Parkinson's disease," Trends Mol Med. Aug. 2003;9(8):360-5.

Spooren et al., "The effect of a subchronic post-lesion treatment with (−)-deprenyl on the sensitivity of 6-OHDA-lesioned rats to apomorphine and d-amphetamine," J Neural Transm. 1999;106(9-10):825-33.

Suwelack et al., "Neuronal expression of the transcription factor Gli1 using the Tα1 α-tubulin promoter is neuroprotective in an experimental model of Parkinson's disease," *Gene Ther.* 11, 1742-52, Dec. 2004.

Van der Weide et al., "N-0437: a selective D-2 dopamine receptor agonist in in vitro and in vivo models," Eur J Pharmacol. Mar. 1, 1988;147(2):249-58.

Vernon et al., "Subtype selective antagonism of substantia nigra pars compacta Group I metabotropic glutamate receptors protects the nigrostriatal system against 6-hydroxydopamine toxicity in vivo.," J Neurochem. Aug. 20, 2007; [Epub ahead of print].

Vu et al., "Pramipexole attenuates the dopaminergic cell loss induced by intraventricular 6-hydroxydopamine," J Neural Transm. 2000;107(2):159-76.

Wardas, "Neuroprotective role of adenosine in the CNS," *Polish J. Pharmacol.* 54, 313-26, 2002.

Yamashita et al., "Effect of amino acid ergot alkaloids on glutamate transport via human glutamate transporter hG1uT-1," J Neurol Sci. Feb. 18, 1998;155(1):31-6.

Yoshioka et al., "The dopamine agonist cabergoline provides neuroprotection by activation of the glutathione system and scavenging free radicals," Neurosci Res. Jul. 2002;43(3):259-67.

Yuan et al., "Neuroprotective and neurotrophic effect of apomorphine in the striatal 6-OHDA-lesion rat model of Parkinson's disease," Brain Res. Nov. 5, 2004;1026(1):95-107.

Zbarsky et al., "Neuroprotective properties of the natural phenolic antioxidants curcumin and naringenin but not quercetin and fisetin in a 6-OHDA model of Parkinson's disease," Free Radic Res. Oct. 2005;39(10):1119-25.

\* cited by examiner

Model Rat Normal Side
3.3 × 20

Model Rat 6-OHDA-Injected Side

HGF-Injected Rat Normal Side
3.3 × 20

HGF-Injected Rat 6-OHDA-Injected Side

FIG. 4

HEPATOCYTE GROWTH FACTOR GENE THERAPY FOR PARKINSON'S DISEASE

TECHNICAL FIELD TO WHICH THE INVENTION BELONGS

The present invention relates to a therapeutic agent for neurodegenerative diseases, which contains an HGF gene as an active ingredient for the therapy of neurodegenerative diseases such as Parkinson's disease, Alzheimer's disease, spino-cerebellar degeneration, disseminated sclerosis, striatonigral degeneration, spino-muscular atrophy (SMA), Huntington's chorea, Shy-Drager syndrome, Charcot-Marie-Tooth disease, Friedreich ataxia, severe adynamia, Willis circle occlusion, amyloidosis, Pick's disease, spinal cord injury, diabetic peripheral neuritis, and ischemic cerebrovascular disorders (cerebral infarction, cerebral hemorrhage, etc.).

BACKGROUND ART

Attempts have been made to use Glial cell line-Derived Neurotrophic Factor (GDNF) that is recognized to exhibit nerve protecting action for the prevention and therapy of neurodegenerative diseases such as Parkinson's disease. However, studies thus far revealed that GDNF has an insufficient effect, so that substances that have more potent nerve protecting action have been demanded for the prevention and therapy of neurodegenerative diseases.

Hepatocyte Growth Factor (HGF) has been found as a potent growth promoting factor for mature hepatocytes and various pharmaceutical activities of it have been reported (Experimental Medicine, Vol. 10, No. 3 (Supplemental Issue) 330-339 (1992)). Further, by making use of its pharmaceutical actions, HGF has been studied and developed as a therapeutic agent for various diseases. On the other hand, the application of an HGF gene to gene therapy has been reported (JP 3-72883 A, WO 97/07824, WO 01/26694).

Actions of HGF on nerves reported based on in-vitro experiments include maintenance of survival and prevention of death of nerve cells of hippocampus neurons, promotion of growth and survival of motor neurons, and maturation and maintenance of survival of dopaminergic neurons, which suggests that the in-vitro action of HGF on nerves is stronger than GDNF.

However, the action of HGF is confirmed only by in-vitro experiments and if some action on nerves is found in-vitro, it cannot be said that nerve protection action is exhibited in-vivo. It has not been studied whether or not HGF has preventive and therapeutic effects on neurodegenerative diseases such as Parkinson's disease.

Further, HGF has a half life in blood as short as about 10 minutes so that it is difficult to maintain its blood level and there has been a problem in the capability of a translocation of an effective amount of HGF to an affected site. The inventor of the present invention has already made it clear that the use of HGF gene in the therapy of various diseases can solve the problems of the half life of HGF and capability of translocation of HGF to the affected site (JP 3-72883 A, WO 97/07824, WO 01/26694).

Therefore, utilization of the HGF gene in the prevention and therapy of neurodegenerative diseases is expected.

DISCLOSURE OF THE INVENTION

It is an object of the present invention to provide a therapeutic method for neurodegenerative diseases such as Parkinson's disease for which no effective remedy has been found and a therapeutic agent for use therein. Specifically, it is an object of the present invention to provide a therapeutic agent for neurodegenerative diseases such as Parkinson's disease, containing the HGF gene as an effective ingredient, a therapeutic method for neurodegenerative diseases such as Parkinson's disease, including administering an HGF gene, and use of the HGF gene in preparing a therapeutic agent for neurodegenerative diseases such as Parkinson's disease.

The inventor of the present invention has made extensive studies and as a result he has found that the HGF gene actually is effective for the prevention and therapy of neurodegenerative diseases such as Parkinson's disease, thereby achieving the present invention.

More specifically, the present invention relates to the following items.

(1) A therapeutic agent for neurodegenerative diseases, including a hepatocyte growth factor (HGF) gene as an active ingredient.

(2) The therapeutic agent according to the item (1), in which the agent is administered to a neurodegenerated site.

(3) The therapeutic agent according to the item (1) or (2), in which the neurodegenerative disease is selected from the group consisting of Parkinson's disease, Alzheimer's disease, spino-cerebellar degeneration, disseminated sclerosis, striatonigral degeneration, spino-muscular atrophy (SMA), Huntington's chorea, Shy-Drager syndrome, spinal cord injury, diabetic peripheral neuritis, and ischemic cerebrovascular disorders.

(4) The therapeutic agent according to the item (3), in which the neurodegenerative disease is selected from the group consisting of Parkinson's disease, Alzheimer's disease, ischemic cerebrovascular disorders, diabetic peripheral neuritis, and spinal cord injury.

(5) The therapeutic agent according to the item (4), in which the neurodegenerative disease is Parkinson's disease.

(6) The therapeutic agent according to the item (2), in which the neurodegenerated site is selected from the group consisting of cerebrum, mesencephalon, cerebellum, spinal cord, medulla oblongata, and peripheral nerve.

(7) The therapeutic agent according to the item (2), in which the neurodegenerated site is selected from the group consisting of the cerebral cortex, striate body, hippocampus, and substantia nigra.

(8) The therapeutic agent according to the item (6) or (7), in which the degenerated nerve is a dopamine neuron.

(9) The therapeutic agent according to any one of the items (1) to (8), in which the HGF gene is incorporated in a plasmid vector or virus vector.

(10) The therapeutic agent according to any one of the items (1) to (8), in which the HGF gene is in the form of a Sendai virus (HVJ)-liposome or a Sendai virus (HVJ)-E (envelope).

(11) The therapeutic agent according to any one of the items (1) to (10), in which the agent is administered several times as needed.

(12) The therapeutic agent according to any one of the items (1) to (11), in which a pharmaceutically effective amount of the gene is used.

(13) A method of treating neurodegenerative diseases, including introducing an HGF gene to a human being.

(14) The method according to the item (13), further including administering the HGF gene to a neurodegenerated site.

(15) The method according to the item (13) or (14), in which the neurodegenerative disease is selected from the group consisting of Parkinson's disease, Alzheimer's disease, spinocerebellar degeneration, disseminated sclerosis, striatonigral degeneration, spino-muscular atrophy (SMA), Huntington's chorea, Shy-Drager syndrome, spinal cord injury, diabetic peripheral neuritis, and ischemic cerebrovascular disorders.

(16) The method according to the item (15), in which the neurodegenerative disease is selected from the group consisting of Parkinson's disease, Alzheimer's disease, ischemic cerebrovascular disorders, diabetic peripheral neuritis, and spinal cord injury.

(17) The method according to the item (16), in which the neurodegenerative disease is Parkinson's disease.

(18) The method according to the item (13), in which the neurodegenerated site is selected from the group consisting of the cerebrum, mesencephalon, cerebellum, spinal cord, medulla oblongata, and peripheral nerve.

(19) The method according to the item (13), in which the neurodegenerated site is selected from the group consisting of the cerebral cortex, striate body, hippocampus, and substantia nigra.

(20) The method according to the item (18) or (19), in which the degenerated nerve is a dopamine neuron.

(21) The method according to any one of the items (13) to (20), in which the HGF gene is incorporated in a plasmid vector or virus vector.

(22) The method according to any one of the items (13) to (20), in which the HGF gene is in the form of a Sendai virus (HVJ)-liposome or a Sendai virus (HVJ)-E (envelope).

(23) The method according to any one of the items (13) to (22), further including administering the HGF gene several times as needed.

(24) The method according to any one of the items (13) to (23), further including administering a pharmaceutically effective amount of the gene.

(25) A use of an HGF gene for manufacturing a therapeutic agent for neurodegenerative diseases.

(26) The use according to the item (25), in which the therapeutic agent for neurodegenerative diseases is administered to a neurodegenerated site.

(27) The use according to the item (25) or (26), in which the neurodegenerative disease is selected from the group consisting of Parkinson's disease, Alzheimer's disease, spino-cerebellar degeneration, disseminated sclerosis, striatonigral degeneration, spino-muscular atrophy (SMA), Huntington's chorea, Shy-Drager syndrome, spinal cord injury, diabetic peripheral neuritis, and ischemic cerebrovascular disorders.

(28) The use according to the item (27), in which the neurodegenerative disease is selected from the group consisting of Parkinson's disease, Alzheimer's disease, ischemic cerebrovascular disorders, diabetic peripheral neuritis, and spinal cord injury.

(29) The use according to the item (28), in which the neurodegenerative disease is Parkinson's disease.

(30) The use according to the item (26), in which the neurodegenerated site is selected from the group consisting of the cerebrum, mesencephalon, cerebellum, spinal cord, medulla oblongata, and peripheral nerve.

(31) The use according to the item (26), in which the neurodegenerated site is selected from the group consisting of the cerebral cortex, striate body, hippocampus, and substantia nigra.

(32) The use according to the item (30) or (31), in which the degenerated nerve includes a dopamine neuron.

(33) The use according to any one of the items (25) to (32), in which the HGF gene is incorporated in a plasmid vector or virus vector.

(34) The use according to any one of the items (25) to (33), in which the HGF gene is in the form of a Sendai virus (HVJ)-liposome or a Sendai virus (HVJ)-E (envelope).

(35) The use according to any one of the items (25) to (34), in which a pharmaceutically effective amount of the HGF gene is used.

Also, the present invention relates to a use of a hepatocyte growth factor (HGF) gene for manufacturing a therapeutic agent for neurodegenerative diseases, and a method of treating neurodegenerative diseases, including administering a pharmacologically effective amount of a hepatocyte growth factor (HGF) gene to a patient.

Further, the present invention relates to a therapeutic agent for a neurodegenerative disease selected from the group consisting of Parkinson's disease, Alzheimer's disease, spinocerebellar degeneration, disseminated sclerosis, striatonigral degeneration, spino-muscular atrophy (SMA), Huntington's chorea, Shy-Drager syndrome, Charcot-Marie-Tooth disease, Friedreich ataxia, severe adynamia, Willis circle occlusion, amyloidosis, Pick's disease, subacute myelo-opticoneuropathy (SMON), dermatomyositis, polymyositis, Creutzfeld-Jakob disease, Behcet's syndrome, systemic lupus erythematosus, sarcoidosis, periarteritis nodosa, ossification of posterior longitudinal ligament, diffuse spinal canal stenosis, mixed connective tissue disease, spinal cord injury, diabetic peripheral neuritis, and ischemic cerebrovascular disorders (including cerebral infarction and cerebral hemorrhage), and to a method for the therapy of the diseases, and a use for manufacturing the therapeutic agent for the diseases.

The neurodegenerative disease may be a disease selected from the group consisting of Parkinson's disease, Alzheimer's disease, spino-cerebellar degeneration, disseminated sclerosis, striatonigral degeneration, spino-muscular atrophy (SMA), Huntington's chorea, Shy-Drager syndrome, spinal cord injury, diabetic peripheral neuritis, and ischemic cerebrovascular disorders.

EMBODIMENT OF THE INVENTION

Hereinafter, the present invention will be described in detail.

"HGF gene" as used herein indicates a gene that can express HGF (HGF protein). Specifically, it includes cDNA of HGF as described in Nature, 342, 440 (1989); JP 2777678 B; Biochem. Biophys. Res. Commun., 163, 967 (1989); Biochem. Biophys. Res. Commun., 172, 321 (1990), etc. incorporated in a suitable expression vector (non-virus vector, virus vector) described later on. Here, the base sequence of DNA that codes for HGF is described in the aforementioned literature and is registered in databases including Gen Bank and the like. Therefore, the cDNA of HGF can be cloned using a suitable DNA part as a primer for PCR based on the aforementioned information of sequence, for example, by performing a RT-PCR reaction of mRNA derived from liver or leucocytes. One skilled in the art can easily perform the cloning according to fundamental textbooks, for example, Molecular Cloning, 2nd Ed., Cold Spring Harbor Laboratory Press (1989) and the like. Further, the HGF gene of the present invention is not limited to those described above and any gene may be used as the HGF gene of the present invention as long as the protein expressed by such a gene has substantially the same action as that of HGF. That is, among 1) DNA that hybridizes with the aforementioned cDNA under stringent conditions, and 2) DNA that codes for a protein with an amino acid sequence having substitution, deletion and/or addition of one or a plurality (1 to 10, preferably 1 to 5, more preferably 1 or 2) of amino acids in the amino acid sequence of the protein coded for by the aforementioned cDNA, and so forth, those DNAs that code for proteins having an activity as HGF are included in the category of the HGF gene of the present invention. In addition, those DNAs that code for subtypes of HGF having HGF-like activity and HGF variants are also included in the HGF gene of the present invention. Examples of the HGF variants include naturally occurring mutants with the deletion of 5 amino acids, expressed as delta5 HGF, and in addition NK2 and NK1. The effect of HGF as used herein refers to the effects of the maintenance of the survival and prevention of death of nerve cells of hippocampus neurons, promotion of growth and survival of motor neurons, and maturation and maintenance of survival of dopaminergic neurons. Here, the aforementioned DNAs 1) and 2) can be obtained with ease by a site-directed mutation inducing method, a PCR method, an ordinary hybridization method or the like. Specifically, these may be performed by referring to fundamental textbooks such as the aforementioned Molecular Cloning and the like.

Now, the introduction method, introduction form, and introduction amount of the gene used in the gene therapy of the present invention will be described in detail.

When a gene therapeutic agent containing an HGF gene as an active ingredient is administered to a patient, its administration forms are roughly grouped into two types, one in which a non-virus vector is used and another in which a virus vector is used. Manuals of experiments and the like describe their preparation method and administration method in detail (Supplementary volume of Experimental Medicine, "Fundamental Technology of Gene Therapy", Yodosha, 1996; Supplementary volume of Experimental Medicine, "Gene Introduction & Experimental Technique for Expression Analysis", Yodosha, 1997; Japan Society of Gene Therapy, ed., "Gene Therapy Development Research Handbook", N.T.S., 1999).

Hereinafter, description will be made in detail.

A. Case of Using a Non-Virus Vector

By using a recombinant expression vector in which a conventional gene expression vector is incorporated, a target gene can be introduced into a cell or tissue by the technique as described below.

Methods of introducing a gene into a cell include a lipofection method, a phosphoric acid-calcium co-precipitation method, a DEAE-dextran method, a DNA direct injection method using a micro glass tube and so forth.

Methods of introducing a gene into a tissue include a gene introduction method by means of an internal liposome, a gene introduction method by means of an electrostatic type liposome, an HVJ-liposome method, an improved HVJ-liposome method (an HVJ-AVE liposome method), a method using an HVJ-E (envelope) vector, a gene introduction method mediated by a receptor, a method in which a DNA molecule together with a carrier (metal particle) is introduced into a cell by using a particle gun, a method of directly introducing naked-DNA, an introduction method by means of a positively charged polymer and the like. Recombinant expression vectors can be incorporated into cells by any one of these methods.

Among them, the HVJ-liposome is obtained by enclosing a DNA in a liposome made of a lipid double layer and fusing the resultant liposome with a Sendai virus (Hemagglutinating virus of Japan: HVJ).

The HVJ-liposome method is featured by a very high activity of fusion with the cell membrane as compared with the conventional liposome method and is a preferable introduction form. The method of preparing an HVJ-liposome is described in detail in the literature (Supplementary volume of Experimental Medicine, "Fundamental Technology of Gene Therapy", Yodosha, 1996; Supplementary volume of Experimental Medicine, "Gene Introduction & Experimental Technique for Expression Analysis", Yodosha, 1997; J. Clin. Invest. 93, 1458-1464 (1994); Am. J. Physiol., 271, R1212-1220 (1996) and so forth) and reference is made thereto. On the other hand, the HVJ liposome method is the method described in, for example, Molecular Medicine, 30, 1440-1448 (1993); Experimental Medicine, 1, 1822-1826 (1994); Protein Nucleic Acid and Enzyme, 42, 1806-1813 (1997) and so forth, preferably the method described in Circulation, 92 (Suppl. II), 479-482 (1995).

HVJ is preferably a Z strain (available from ATCC). Basically, other HVJ strains (for example, ATCC VR-907, ATCC VR-105, etc.) can also be used.

The HVJ-E (envelope) vector is one obtained by introducing an inactivated exogenous gene into a Sendai virus envelope and can be prepared according to the description of WO 01/57204.

Further, the direct introduction method of naked-DNA is the simplest technique among the aforementioned techniques and in this respect is a preferable introduction method.

The expression vector as used herein may be any expression vector as long as it can express the target gene in an organism. Examples of such an expression vector include pCAGGS (Gene 108, 193-200 (1991)), pBK-CMV, pcDNA3.1, pZeoSV (Invitrogen Corporation, Stratagene), and pVAX1.

B. Case of Using a Virus Vector

Methods of using virus vectors such as recombinant adenovirus and retrovirus are typical methods. More specifically, a target gene can be introduced into a DNA virus or RNA virus, for example, neutralized retrovirus, adenovirus, adeno-associated virus, herpes virus, vaccinia virus, pox virus, polio virus, sindbis virus, Sendai virus, SV40, immune deficiency disease virus (HIV) and so forth to have a cell infected with a recombinant virus to thereby introduce the gene into the cell.

It has been known that among the aforementioned virus vectors, the adeno virus shows an infection efficiency higher than that when using any other virus vectors and in this respect, it is preferable that an adeno virus vector system be used.

The method of introducing the gene therapeutic agent of the present invention into patients includes an in-vivo method in which the gene therapeutic agent is directly introduced in the body and an ex-vivo method in which the gene therapeutic agent is introduced to a certain cell removed from a human outside the body and then the cell is returned into the body (see Nikkei Science, April, 1994, pages 20 to 45; Gekkan Yakuji (Monthly Pharmaceutical Affairs), 36(1), 23-48

(1994); Experimental Medicine Supplemental Issue, 12(15), (1994); The Japan Society of Gene Therapy, ed., "Handbook of Gene Therapy Development Research", N.T.S., 1999). In the present invention, the in-vivo method is preferable.

Various dosage forms that match the aforementioned respective forms of administration (for example, liquid agents) may be adopted. For example, an injectable solution containing a gene as an active ingredient is adopted, the injectable solution may be prepared by a conventional method; for example, it can be prepared by dissolving the gene in an appropriate solvent (a buffer such as PBS, physiological saline, sterilized water or the like), sterilizing by passing the solution through a filter or the like as necessary, and then filling the sterilized solution in a germ-free vessel. The injectable solution may contain a conventional carrier and the like as necessary. Liposomes such as an HVJ-liposome may be provided in the form of liposome preparations such as suspensions, frozen preparations, and centrifuge-concentrated frozen preparations. An HVJ-liposome may be prepared according to the disclosure of WO 01/32220, WO 01/26694 and the like.

The diseases as mentioned herein refer to those diseases accompanied by neurodegeneration, including various diseases such as those in which disorders of nerve cells proceed progressively and those caused by external injury or other diseases. Among them, so-called incurable nervous diseases that occur rarely are included. Although the nervous diseases occur by various causes and in various sites or nerves, repairing of the degenerated nerve itself and improvement of its function by the therapeutic agent of the present invention indicate that the therapeutic agent of the present invention is effective in the therapy and improvement of the disease accompanied by various types of neurodegeneration. The diseases to which the present invention is applicable include nervous diseases such as Parkinson's disease, Alzheimer's disease, spino-cerebellar degeneration, disseminated sclerosis, striatonigral degeneration, spino-muscular atrophy (SMA), Huntington's chorea, Shy-Drager syndrome, Charcot-Marie-Tooth disease, Friedreich ataxia, severe adynamia, Willis circle occlusion, amyloidosis, Pick's disease, subacute myelo-optico-neuropathy (SMON), dermatomyositis, polymyositis, Creutzfeld-Jakob disease, Behcet's syndrome, systemic lupus erythematosus, sarcoidosis, periarteritis nodosa, ossification of posterior longitudinal ligament, diffuse spinal canal stenosis, mixed connective tissue disease, spinal cord injury, diabetic peripheral neuritis, and ischemic cerebrovascular disorders (cerebral infarction, cerebral hemorrhage, etc.). All of the diseases are accompanied by neurodegeneration. For example, Parkinson's disease is accompanied by the degeneration of the mesencephalon dopamine neuron; Alzheimer's disease is accompanied by the degeneration of the cerebral cortex and hippocampus; spinal cord injury is accompanied by the degeneration of the motor nerve and sensory nerve of the spinal cord; diabetic peripheral neuritis is accompanied by the degeneration of the sensory nerve; ischemic cerebrovascular disorders (cerebral infarction, cerebral hemorrhage, etc.) are accompanied by the degeneration of the cerebral cortex and hippocampus; spino-cerebellar degeneration is accompanied by the degeneration of the cerebellum; disseminated sclerosis is accompanied by the degeneration of the nerve sheaths of the cerebrum, mesencephalon, cerebellum, medulla oblongata and the like; striatonigral degeneration is accompanied by the degeneration of the striate body, substantia nigra, frustule, caudate nucleus, etc. of the cerebellum, spinal cord and the like; spino-muscular atrophy is accompanied by the degeneration of the motor nerve of the spinal cord; Huntington's chorea is accompanied by the degeneration of the cerebral basal ganglia; myodystrophy is accompanied by the degeneration of the cerebrum and spinal cord; Pick's diseases is accompanied by the degeneration of the cerebrum; and Shy-Drager syndrome is accompanied by the degeneration of the spinal cord, autonomic nerve ganglion, cerebellum, extrapyramidal tract, pyramidal tract, etc. The gene therapy agent of the present invention can be used and is effective in the therapy and alleviation of the symptoms for not only those patients who suffer from severe nervous diseases but also those patients who suffer from mild nervous diseases.

The gene therapy agent of the present invention is administered by an appropriate administration method to an appropriate administration site selected depending on the target disease, symptom, etc. to be treated. For example, it is advisable that the gene therapy agent of the present invention be administered to the cerebrum for those diseases that are accompanied mainly by degeneration of the cerebrum. It may be administered to the striate body for those diseases that are accompanied by local striatal degeneration. It may as well be administered systemically for those patients who suffer from systemic neurodegeneration. The administration is performed preferably by an appropriate method such as injection. The gene therapy agent of the present invention is preferably administered around sites where neurodegeneration occurred, and in arteries and veins, for example, by administration in the brain, administration in the spinal cord, etc.

As the neurodegenerated site, for example, Parkinson's disease involves the site of mesencephalon dopamine neurons; Alzheimer's disease involves the site of the cerebral cortex and hippocampus; spinal cord injury involves the site of motor nerves and sensory nerves of the spinal cord; diabetic peripheral neuritis involves the site of the degeneration of sensory nerves; ischemic cerebrovascular disorders (cerebral infarction, cerebral hemorrhage, etc.) involve the site of the cerebral cortex and hippocampus; spino-cerebellar degeneration involves the site of the cerebellum; disseminated sclerosis involves the site of the nerve sheaths of the cerebrum, mesencephalon, cerebellum, medulla oblongata and the like; striatonigral degeneration involves the site of the striate body, substantia nigra, frustule, caudate nucleus, etc. of the cerebellum, spinal cord and the like; spino-muscular atrophy involves the site of the motor nerve of the spinal cord; Huntington's chorea involves the site of the cerebral basal ganglia; myodystrophy involves the site of the cerebrum and spinal cord; Pick's diseases involves the site of the cerebrum; and Shy-Drager syndrome involves the site of the spinal cord, autonomic nerve ganglion, cerebellum, extrapyramidal tract, pyramidal tract, etc. A therapeutic effect can be exerted on the neurodegenerative diseases by administering the HGF gene to the neurodegenerated site and its vicinities, or a wide portion including the neurodegenerated site.

For example, in the therapy of Parkinson's diseases, the gene therapy agent of the present invention may as well be administered to the striate body directly.

A pharmaceutically effective amount of the therapy agent of the present invention is administered to the patients. Here, "a pharmaceutically effective amount is administered" as used herein means that a sufficient amount of the HGF gene for generating a polypeptide or protein at an appropriate level for the therapy of the neurodegenerative disease is administered to the patient. Specific dosages, which may differ depending on the symptoms and the like of patients, is selected from the range of about 1 µg to about 50 mg, preferably about 10 µg to about 5 mg, more preferably about 50 µg to about 5 mg as the HGF gene per adult patient.

The therapeutic agent of the present invention is preferably administered once every few days or every few weeks, although the number of times of administration may be changed as appropriate depending on the symptoms of the patients. The therapeutic agent of the present invention is used for noninvasive administration. Hence, the present invention has a feature that the agent can be administered several times according to the symptoms of the patient.

Hereinafter, the present invention will be described in detail by examples. However, the present invention should not be considered to be limited by the examples.

The present invention prevents the degeneration and lesion of dopamine neurons by pre-administering HGF as shown particularly in the examples. Parkinson's disease, which is chronic and progressive, can be retarded in progress or suppressed by the administration of HGF due to its protecting activity for dopamine neurons; thus HGF acts as a preventive and therapeutic agent for Parkinson's disease. Further, HGF is useful as a therapeutic agent for diseases caused by nervous injury, including neurodegenerative diseases such as Alzheimer's disease, spinal injury, ischemic cerebrovascular disorder, peripheral neuritis and so forth.

BRIEF DESCRIPTION OF THE DRAWINGS

FIGS. 2, 3 and 4 each include four photographs, which photographs show normal sides and 6-OHDA-injected sides in a model rat group and HGF-administered group, respectively. FIGS. 2, 3 and 4 differ from each other only in magnification.

EXAMPLES

Example 1

Therapy of Parkinson's Disease with HGF

By using Parkinson's disease model rats, the effect of HGF on model rats was examined praxiologically and histologically.

The drug-induced Parkinson's disease model rats used were 4-week-aged male Wister rats weighing about 100 g. 10 µl (100 µg) of HGF plasmid was injected to two sites of the striate body of each Wister rat (5 µl each to two sites). Control rats used were Wister rats injected with the same amount of β-gal.

After 5 days from the injection, 3 µl (9 µg) of 6-OHDA (6-hydroxydopamine), which is a neurotoxin that specifically destroys dopamine neurons, was injected into the nigra macula densa in the mesencephalon.

After 2, 4, 6, 8, and 10 weeks, respectively, from the injection of 6-OHDA, five animals each from the normal rat group, model rat group, control rat group that was injected with β-gal, and HGF-injected group were observed for gyration. Here, the normal rat group included untreated normal rats, the model rat group included Parkinson's disease model rats whose nigra macula densa was administered with 6-OHDA, the control group included rats that were injected with 6-OHDA after the injection of β-gal, and the HGF-injected group included rats injected with 6-OHDA after the injection of HGF.

The gyration was induced by intraperitoneally injecting 5 mg/kg rat of amphetamine (or apomorphine) to the rats of each group after 2, 4, 6, 8, and 10 weeks, respectively, from the injection of 6-OHDA. Here, amphetamine releases dopamine from dopamine neurons. However, on the 6-OHDA-injected side, no release of dopamine occurs in the striate body because the nerve termini are destroyed there, so that only the striate body on the normal side is stimulated, causing gyration to the injured side.

After 8 weeks, the brains were removed from the rats of each group and subjected to immune staining with anti-TH (tyrosine hydroxylase) antibody. Here TH is a rate-limiting enzyme of catecholamine and serves as an indicator for dopamine neurons. Cells at five sites on the substantia nigra in the rats of each group were counted and the survival ratio of dopamine neurons as compared with normal substantia nigra was calculated.

The observation of gyration gave the following results.

Figure 1:
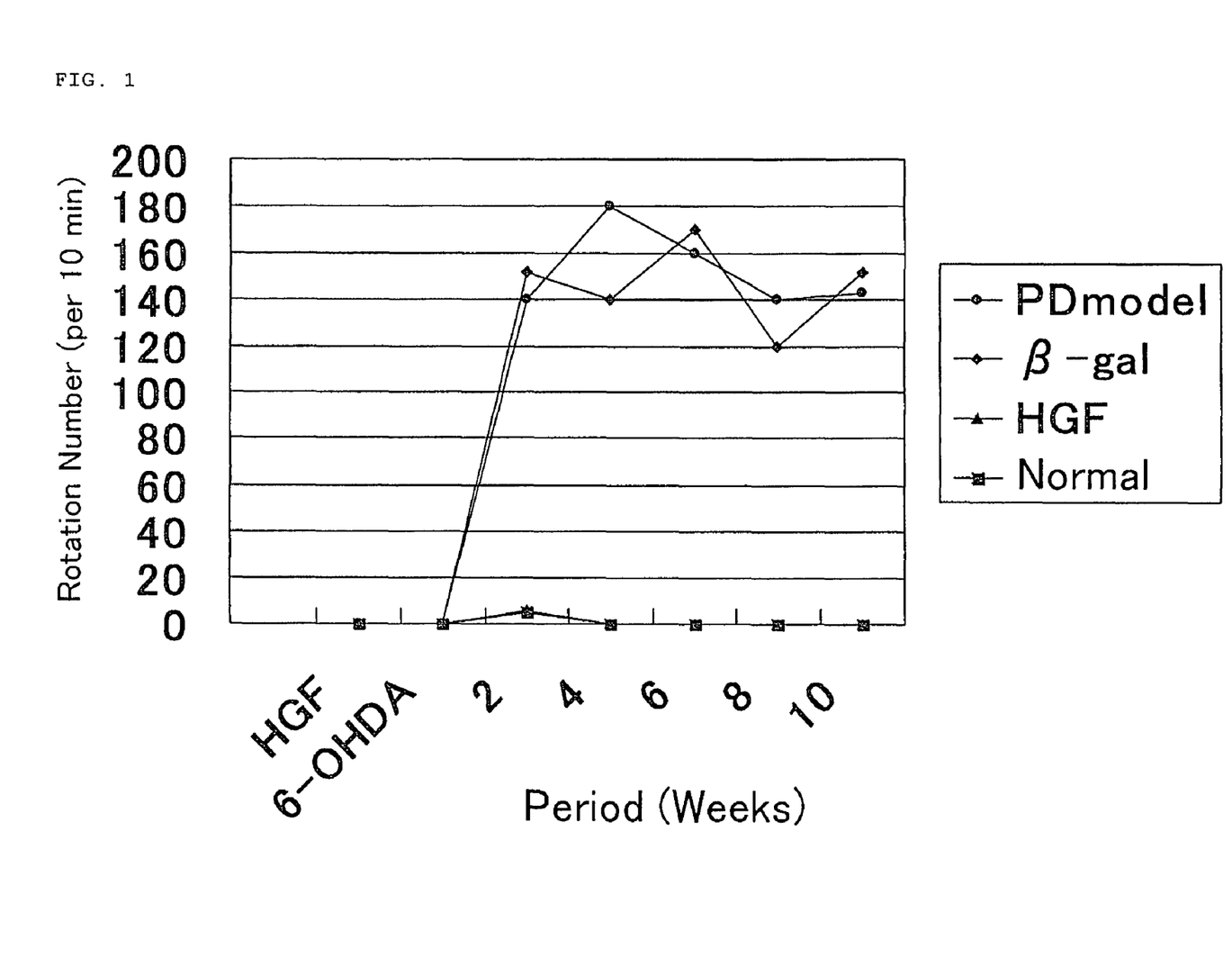
FIG. 1 is a diagram showing an effect of HGF on gyration induced by an amphetamine (change in gyration).

The control group injected with β-gal, like the Parkinson's disease model group, showed abnormal gyration. The HGF-administered group showed substantially no gyration, which was the same state as the normal rats (FIG. 1). The excitability caused by the stimulation of amphetamine (bristling of hair, sensitive to sounds or noises) was observed for any of the rat groups. The results indicate that pre-administration of HGF protected the substantia nigra dopamine neurons in the mesencephalon from 6-OHDA, neurotoxin, thus suppressing the symptoms of the Parkinson's disease model rats.

The symptom of Parkinson's disease is said to appear when the level of the substantia nigra dopamine neurons decreases to 20% or less of the normal level. When the level of the substantia nigra dopamine neurons decreases to 10% or less of the normal level in the model animals, unique behavior such as abnormal gyration appears.

The results of the histological examination were as follows.

Figure 2:
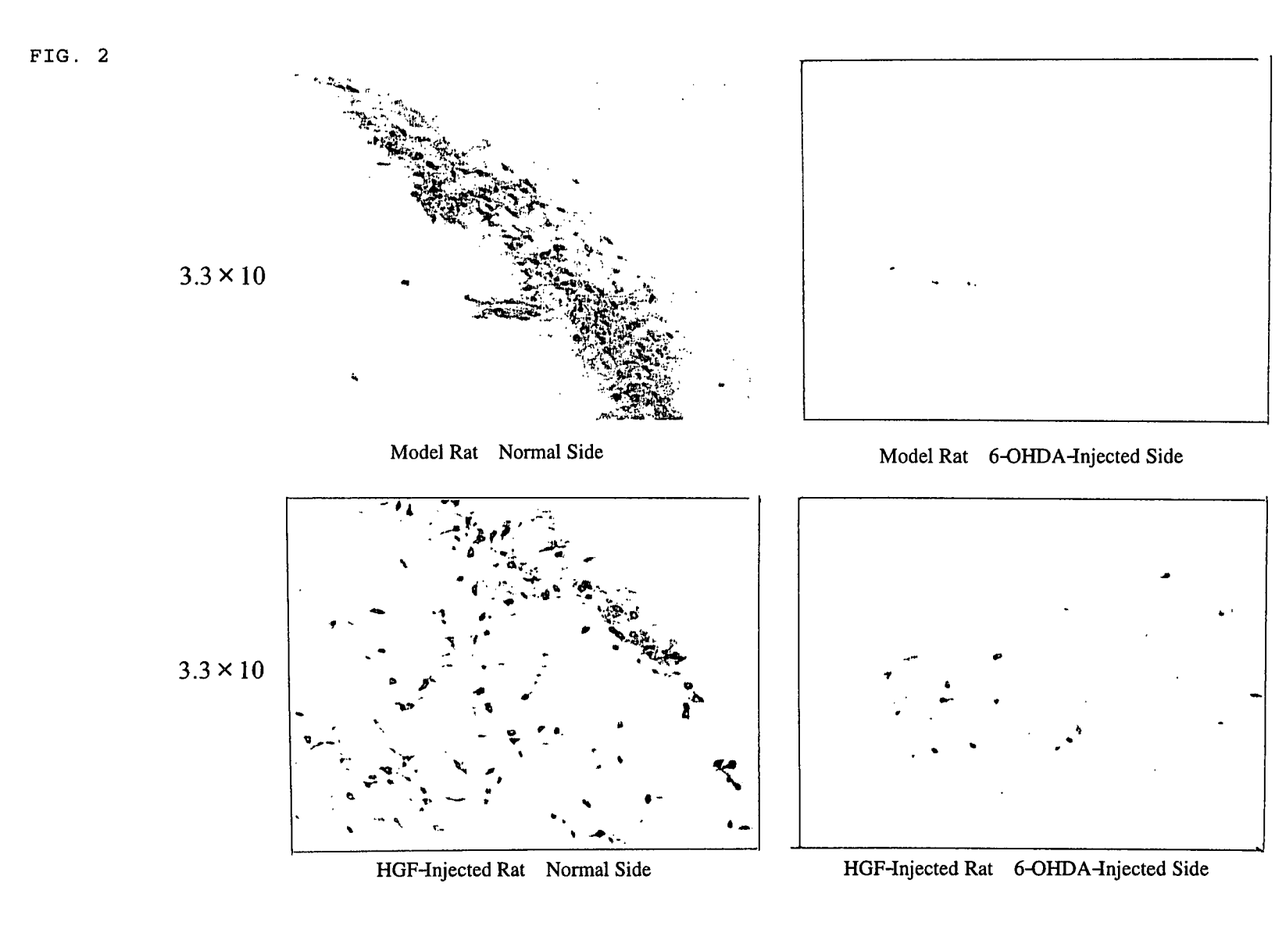
FIG. 2 is a diagram showing the nerve-protecting effect by HGF in a Parkinson's disease model rat (magnification: 3.3× 10 (magnification of eyepiece×magnification of objective)).
Figure 3:
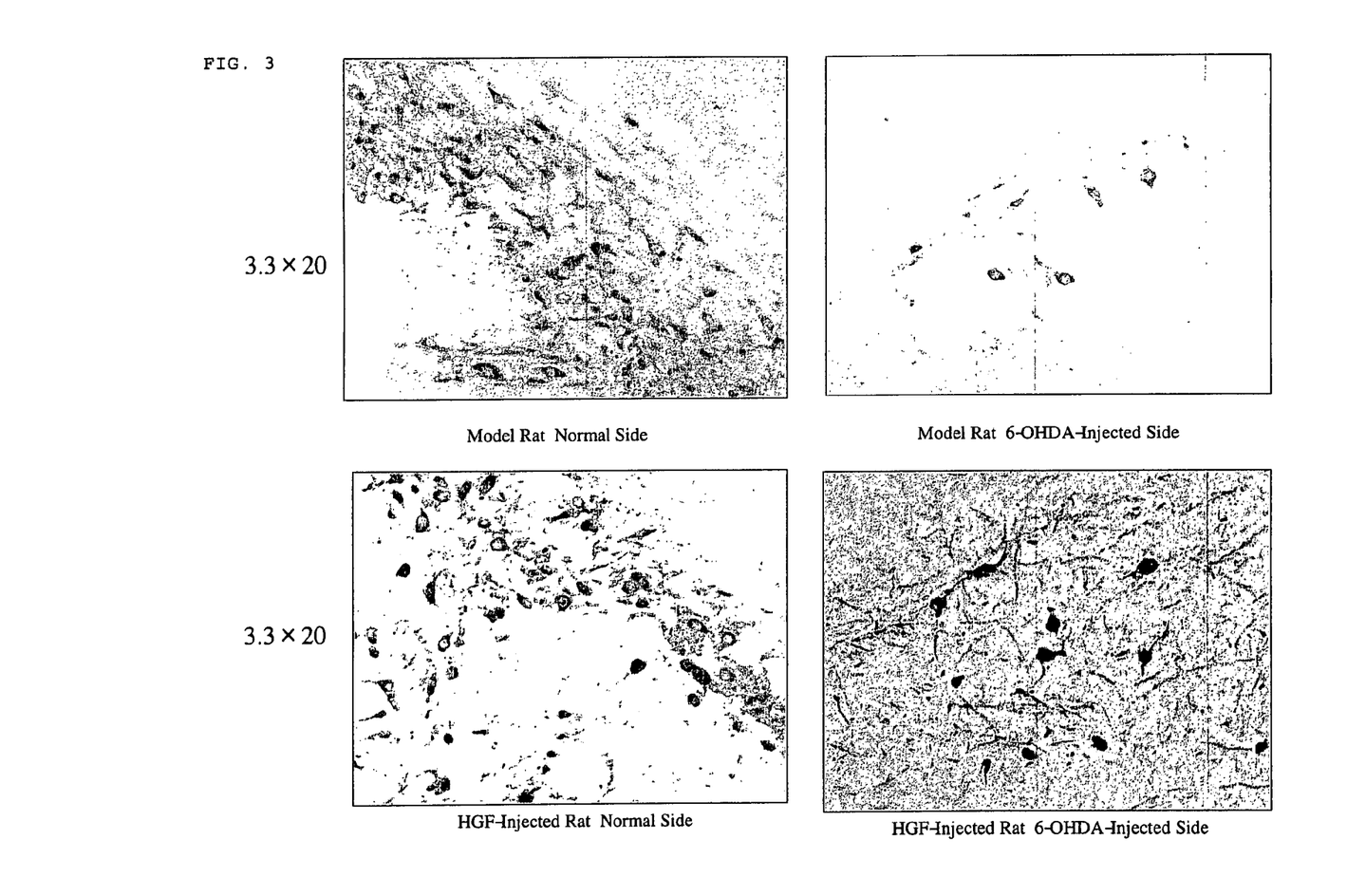
FIG. 3 is a diagram showing the nerve-protecting effect by HGF in a Parkinson's disease model rat (magnification: 3.3× 20 (magnification of eyepiece×magnification of objective)).
Figure 4:
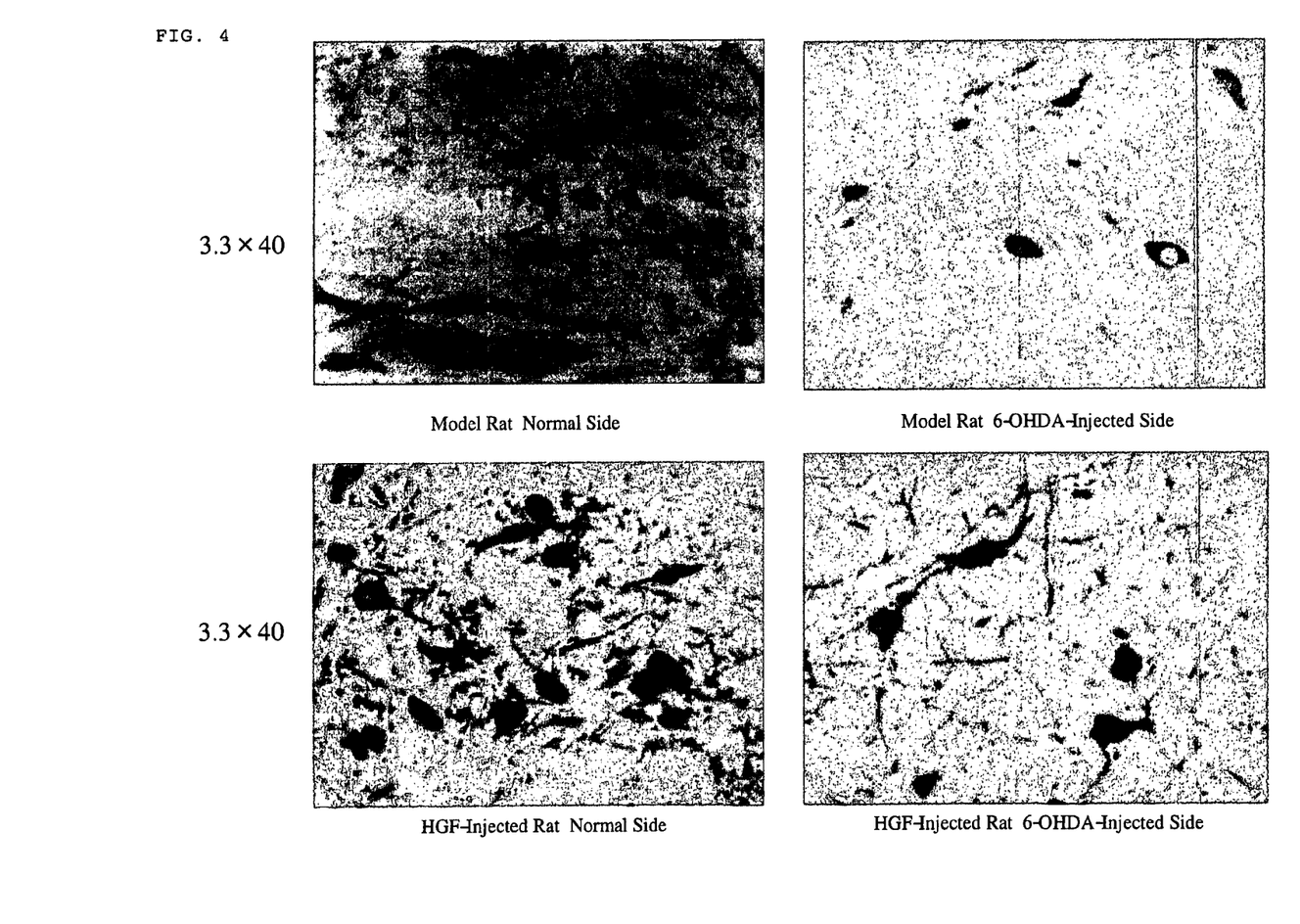
FIG. 4 is a diagram showing the nerve-protecting effect by HGF in a Parkinson's disease model rat (magnification: 3.3× 40 (magnification of eyepiece×magnification of objective)).

As compared with normal substantia nigra, almost all the substantia nigra cells were degenerated or dead in the model rats having substantia nigra injected with 6-OHDA, neurotoxin (see FIGS. 2 to 4, showing the results of observations at different magnifications, respectively). Observation of several eyefields and counting the number of survival cells resulted in a cell survival ratio of a few percent to about 10% of the normal substantia nigra. In the HGF-injected group, the survival cell ratio was 20 to 30%, which corresponded to the abnormal gyration. In addition, HGF injected into normal substantia nigra gave no effect on the normality of the cells.

Example 2

Effect of HGF on Repairing Nerves

The effect of HGF on regeneration and repairing of substantia nigra dopamine neurons in the mesencephalon was examined.

3 µl (9 µg) of 6-OHDA was injected into the substantia nigra macula densa in the mesencephalon of Wister rats and then 10 µl (100 µg) of HGF plasmid was injected into the striate body at two sites thereof (5 µl each to two sites). On this occasion, Wister rats injected with β-gal were used as control rats.

The invention claimed is:

1. A method of reducing dopaminergic cell death, comprising administering directly to the striate body of a subject in need thereof a pharmacologically effective amount of an expression vector which encodes and expresses hepatocyte growth factor (HGF), whereby dopaminergic cell death is reduced.

2. The method of claim 1 wherein the subject is a rat.

3. The method of claim 1 wherein the subject is a human.

4. The method of claim 1 wherein the plasmid is injected to two sites in the striate body.

5. The method of claim 1 wherein the expression vector is pCAGGs.

6. The method of claim 1 wherein the expression vector is pBK-CMV.

7. The method of claim 1 wherein the expression vector is pcDNA3.1.

8. The method of claim 1 wherein the expression vector is pZeoSV.

9. The method of claim 1 wherein the expression vector is pVAX1.

10. The method of claim 1 wherein the pharmacologically effective amount is in the range of about 1 µg to about 50 mg.

11. The method of claim 1 wherein the pharmacologically effective amount is in the range of about 10 µg to about 5 mg.

12. The method of claim 1 wherein the pharmacologically effective amount is in the range of about 50 µg to about 5 mg.

* * * * *